(12) United States Patent  (10) Patent No.: US 8,583,223 B2
Maddess et al.  (45) Date of Patent: Nov. 12, 2013

(54) ASSESSMENT OF NEURAL FUNCTION

(75) Inventors: Ted Maddess, Kaleen (AU); Andrew James, Cambell (AU)

(73) Assignee: The Australian National University, Australian Capital Territory (AU)

( * ) Notice: Subject to any disclaimer, the term of this patent is extended or adjusted under 35 U.S.C. 154(b) by 0 days.

(21) Appl. No.: 10/581,003

(22) PCT Filed: Nov. 29, 2004

(86) PCT No.: PCT/AU2004/001656
§ 371 (c)(1),
(2), (4) Date: Sep. 13, 2007

(87) PCT Pub. No.: WO2005/051193
PCT Pub. Date: Jun. 9, 2005

(65) Prior Publication Data
US 2008/0108908 A1  May 8, 2008

(30) Foreign Application Priority Data
Nov. 28, 2003  (AU) ................................. 2003906589

(51) Int. Cl.
*A61B 5/04*  (2006.01)
(52) U.S. Cl.
USPC ........................................................ 600/544
(58) Field of Classification Search
USPC ................................................. 600/544, 545
See application file for complete search history.

(56) References Cited

U.S. PATENT DOCUMENTS

| 4,094,307 | A | 6/1978 | Young, Jr. | |
|---|---|---|---|---|
| 4,846,567 | A | 7/1989 | Sutter | |
| 5,474,081 | A * | 12/1995 | Livingstone et al. | 600/544 |
| 6,315,414 | B1 | 11/2001 | Maddess et al. | |
| 6,475,162 | B1 | 11/2002 | Hu | |
| 6,743,183 | B1 * | 6/2004 | Thornton | 600/559 |
| 2003/0013981 | A1 * | 1/2003 | Gevins et al. | 600/544 |
| 2003/0032894 | A1 | 2/2003 | Hu et al. | |
| 2003/0109799 | A1 | 6/2003 | Brown | |
| 2003/0163060 | A1 * | 8/2003 | Maddess et al. | 600/544 |

FOREIGN PATENT DOCUMENTS

| JP | 2003-527913 | 9/2003 |
|---|---|---|
| WO | WO 99/49776 A1 | 10/1999 |
| WO | WO 01/10298 A2 | 2/2001 |
| WO | WO 01/39659 A1 | 6/2001 |
| WO | WO 01/72211 A1 | 10/2001 |
| WO | WO 01/87147 A2 | 11/2001 |

OTHER PUBLICATIONS

Japanese Office Action dated May 18, 2010 (and English translation).
European Search Report dated Jan. 15, 2010.

(Continued)

*Primary Examiner* — Patricia Mallari
*Assistant Examiner* — Christian Jang
(74) *Attorney, Agent, or Firm* — Wood, Phillips, Katz, Clark & Mortimer

(57) ABSTRACT

Assessment of one of the sensory nervous systems of a human subject using patterns of null and non-null stimuli. Parts of the visual system for example, are presented with two simultaneous sequences of stimuli. Each sequence is varied over time between a null stimulus and one or more less frequent non-null stimuli. The variation of each sequence is also controlled so that neighboring parts of the sensory system are less likely to receive simultaneous non-null stimuli. The stimuli are therefore sparse both in time and in some other aspect, typically a spatial dimension. One or more responses of the subject are measured and weight functions are determined for assessment of the sensory system.

23 Claims, 13 Drawing Sheets

(56) References Cited

OTHER PUBLICATIONS

Figure 1:
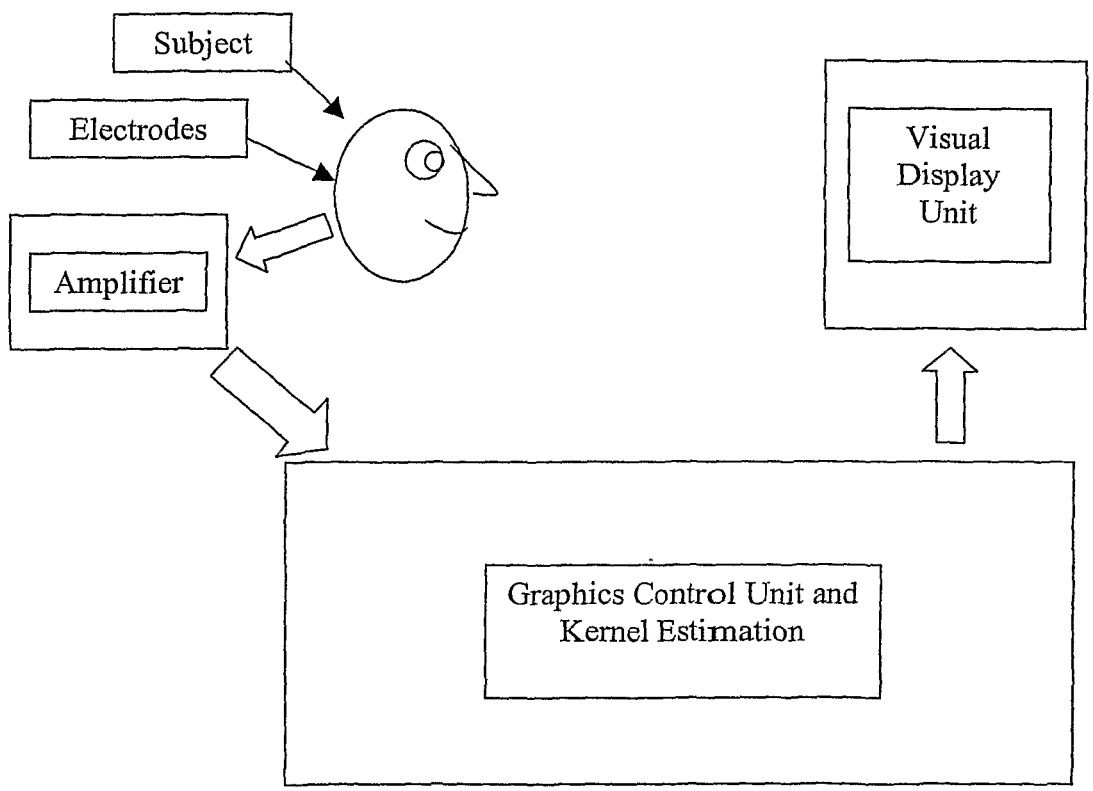

Australian Examiner's Second Report, Aug. 24, 2010—IP Australia.
Japanese Examiner's Second Report, Nov. 9, 2010—Japan Patent Office—and English translation.
Canadian Intellectual Property Office—Office Action dated Jan. 4, 2012.
Examiner's First Report dated Jul. 31, 2009 from the Australian Patent Office (IP Australia).
Supplemental European Search Report dated Sep. 11, 2009.

* cited by examiner

Type I

Type II

ASSESSMENT OF NEURAL FUNCTION

FIELD OF THE INVENTION

This invention relates generally to assessment of the function of the nervous system. More particularly, the present invention concerns a method and apparatus for assessing neural function by spatially sparse stimuli with particular application to diseases affecting the sensory nervous system such as glaucoma, or diseases affecting nerve conduction such as multiple sclerosis, or diseases affecting interpretation of stimuli that are crowded across some sensory dimensions such as the interpretation of collections of letters in reading dyslexia or amblyopia.

BACKGROUND OF THE INVENTION

Nervous system function is commonly assessed by recording evoked potentials (EPs) in response to some stimulus. The EP is a voltage that reflects some combination of the electrical activity of large number of neurones that contribute to the response by being sufficiently close to the recording electrodes. The stimulus is often presented several times and the average response to the stimulus is computed. More recently alternative monitoring means for recording stimulus evoked responses (SERs) have come into practice, including changes in magnetic fields or optical signals generated by neural activity. Another response generated by the nervous system providing possible utility is the pupillary response. Similarly the electro-oculogram, or eye movements measured in other ways, could be used to derive a SER. Functional magnetic imaging can also quantify brain responses to produce an SER. Effects of the scattering, refraction or absorption of infrared radiation or T-rays reflecting neural activity might also be useful in producing SERs. The relatively non-invasive measurement provided by these recording means is desirable in the clinical setting. Evoked electrical potentials reflecting brain activity are easily recorded from electrodes placed upon the scalp. Magnetic, and infrared signals related to neural activity can be similarly recorded through the skin. In the case of monitoring means involving electromagnetic radiation such as infrared or T-rays it may be necessary to project these optical signals into the nervous system and then observe the effects of absorption, refraction or scattering or some collection of these parameters. A potential drawback of surface measurements, or eye movements, or the pupillary response is that, however they are measured, these evoked responses typically represent the collective activity of many neurones in response to the stimulus.

Monitoring means such as the relatively slow infrared method of Takahashi K., Ogata S., Atsumi Y., Yamamoto R., Shiotsuka S., Maki A., Yamashita Y., Yamamoto T., Koizumi H., Hirasawa H., and Igawa M., entitled "Activation of the visual cortex imaged by 24-channel near-infrared spectroscopy", published in Journal of Biomedical Optics, volume 5, pages 93-96, would be useful. Monitoring means involving infrared signals that are biased towards measuring the rapid signals of the type described by: WOLF, M., WOLF, U., CHOI, J. H., GUPTA, R., SAFONOVA, L. P., PAUNESCU, L. A., MICHALOS, A. & GRATTON, E. (2002), entitled "Functional frequency-domain near-infrared spectroscopy detects fast neuronal signal in the motor cortex", published in Neuroimage, volume 17, pages 1868-1875, are preferred as they provide high temporal resolution of neural activity.

Diseases affecting the nervous system may differentially impair component parts of the nervous system. For example separate parts of the retina are differentially affected by the common eye disease glaucoma. These changes to the retina result in localised decreases in visual performance in particular parts of the visual field. Another common neurological disease, multiple sclerosis, causes damage to small regions along myelinated nerves and neural pathways within the brain. Thus, in such cases it would be useful to test neural function with multiple stimuli concurrently in time, each stimulus testing a different component part of the nervous system, with or without some overlap in the stimulated domains, in what might be called Multi-stimulus Evoked Responses (MSERs). The ability to record responses to concurrently presented stimuli to different component parts of the nervous system would clearly reduce some of the problems inherent in classic methods for recording evoked responses, in that the responses would represent the activity of component parts of the nervous system rather than the massed response of some or all the stimulated parts. In the case of testing the visual field, a MSER would allow stimuli to be concurrently presented to multiple parts of the visual field. This would in principle allow more time-efficient mapping of the visual field. As few as one recording sensor placed on or near the eye or scalp could be used, thus making the time required to set up the monitoring means quite short. Thus, the problems of recording evoked responses in the clinic are reduced when responses to stimuli to multiple parts of the nervous system can be recorded by relatively few sensors. Of course this does not preclude the use of many sensors, the possibility of relatively few sensors is simply noted as a possibly useful feature of MSERs.

While some MSER methods have been proposed, the emphasis in the design of the stimulus sequences used to date has most often been to reduce the computational load when estimating the responses, largely by reducing the degree of correlation between the concurrently presented stimulus sequences. For example, Wiener, N ("Nonlinear problems in random theory", New York, Wiley, 1958) proposed the use of continuous Gaussian distributed white noise sequences that in principle could be applied at the temporal modulation functions of the multiple stimuli presented for measurement of MSERs. Sutter, E (U.S. Pat. No. 4,846,567) proposed the use of special stimulus sequences called m-sequences where the stimulus sequence fluctuates between one of two levels in a strictly defined way. These two level m-sequences are a subset of a class of sequences that are said to be binary. These binary sequences vary between two about equally likely stimulus conditions and thus, unlike the stimuli proposed hereafter, never contain a null condition and are not sparse in the sense presented herein. Neither of the stimuli of Wiener or Sutter is designed to optimise responses from any particular part of the nervous system. Stimuli that permit the measurement of MSERs but which are optimised for assessing clinically relevant signals from the nervous system would be potentially more useful.

Of particular interest in assessment of neural function may be those parts of the nervous system that dynamically adapt to prevailing stimulus conditions by using what we will call response-regulating mechanisms. These neural systems are interesting from the point of view of studying neural performance because these response-regulating systems are often complex and strictly controlled. Thus, neural dysfunction might be readily observed in neural systems exhibiting strong response-regulating mechanisms. At the same time appropriate design of stimulus sequences might permit neural systems with response-regulating systems to produce larger and or more reliable responses. An example of response regulation of particular relevance to measuring the visual field by MSER methods is so called lateral masking, which occurs when many stimuli are present in the visual field at the same time. When the stimuli are near to each other the sensitivity to each of the stimuli is reduced, particularly in peripheral vision. In some neurological disorders like amblyopia or reading dyslexia lateral masking appears to operate in an abnormal way, so aside from undoing the potentially deleterious effects of lateral masking it is desirable to construct MSER stimuli that might enhance features of lateral masking for the purposes of studying it directly as a means of characterising diseases specifically effecting lateral masking.

SUMMARY OF THE INVENTION

It is an object of the invention to provide for improved assessment of sensory nervous systems in human subjects, or at least to provide an alternative to existing systems.

Accordingly in one aspect the invention may broadly be said to consist in a method of assessing a sensory nervous system of a subject, including: simultaneously presenting two or more parts of the sensory system with respective sequences of stimuli, varying each sequence over time between a null stimulus and one or more less frequent non-null stimuli, controlling the variation of each sequence so that neighbouring parts of the sensory system are less likely to receive simultaneous non-null stimuli, measuring one or more simultaneous responses by the subject to the sequences of stimuli, and determining weight functions from the responses for assessment of the sensory system.

A null stimulus is one that if presented on its own would evoke no response, such as an image contrast of zero when assessing a visual sensory system. The temporally modulated stimuli should be sufficiently complex so as to permit estimation of some or all of the coefficients of linear and non-linear weighting functions characterising the measured responses to each stimulus presented to each part of the nervous system. Preferably the sequences of stimuli are statistically independent. The responses are generally linear or nonlinear functions of the stimuli and the weight functions may be Wiener or Volterra kernels.

Preferably the non-null stimuli appear in each sequence at a rate of about 0.25 to 25 per second, more preferably at about 0.25 to 6 per second, or 1 to 4 per second. Preferably the probability of neighbouring parts in the sensory system having simultaneous non-null stimuli is zero. The parts of the sensory system receiving stimuli may form a region divided into classes and only one of the classes has a non-zero probability of receiving stimuli at any time. The parts of the sensory system may be in the retina, the ears, the skin, or in the brain of the subject. The stimuli may be selected from a range of signals such as light or sound frequency, or pressure.

In one embodiment the sensory system is a visual system and multiple parts of a retina are presented with stimuli. The sequences may include either binocular or dichoptic stimuli. In another embodiment the sensory system is an aural or tactile system and the ears or skin are presented with stimuli.

In another aspect the invention may be said to consist in apparatus for assessing a sensory nervous system of a subject, including: a stimulator that simultaneously presents two or more parts of the sensory system with respective sequences of stimuli, a monitor that measures one or more simultaneous responses by the subject to the sequences of stimuli, and a processor that varies each sequence over time between a null stimulus and one or more less probable non-null stimuli, controls the variation of each sequence so that neighbouring parts of the sensory system are less likely to receive simultaneous non-null stimuli, and determines weight functions from the responses for assessment of the sensory system.

The sensory system is typically a visual, aural or tactile system and the stimulator presents optical patterns to the eyes, ears or skin of the subject. Preferably the monitor measures responses to the stimuli by way of electrode potentials on the head of the subject.

The present invention arises in part from the discovery that when measuring MSERs response sizes and reliability can be improved by insuring that concurrently presented stimuli are separated in space, thus such stimuli are said to be spatially sparse. This spatially sparse presentation minimises the deleterious effect of lateral masking, thereby increasing the reliability of the multi-stimulus evoked responses. This invention is an extension of a previous application by James A C and Maddess T (International Application Number: PCT/AUO1/00343). That application covered the utility of temporally sparse stimuli for MSERs. Temporally Sparse stimuli consist of temporal sequences of stimulus conditions presented against a baseline null stimulus condition, where the non-null stimulus condition, or conditions, are presented relatively infrequently. In MSER measurement of the visual field it is common for the plurality of stimuli to be presented to multiple regions forming a contiguous array or ensemble of stimulus regions covering a large portion of the visual field. For the older binary stimulus methods for MSERs, adjacent regions in space are simultaneously active, that is, for each region each of its neighbours appears in one of two active stimulus conditions. Notice that by introducing null stimuli between active stimulus conditions temporally sparse stimuli admit the possibility that, on any time step, two or more spatially adjacent stimuli could have many possible spatial arrangements of null and non-null stimuli. That is they could have a spatial neighbour in the plurality of stimuli that was in a non-null stimulus condition, or one that was a null stimulus condition.

Temporally sparse stimuli should be presented at a different positions in the non-temporal dimensions of the plurality of stimuli are arranged so that when any non-null stimulus appears at one location within the plurality that it should have a low probability of having a near neighbour within the plurality that is also a non-null stimulus, and so by implication any non-null stimulus presented within the plurality should by preference have neighbouring stimuli that display null stimuli on the same time step. Making the temporally sparse sequences also be spatially sparse provides an even greater enhancement of MSER reliability than is afforded by temporal sparseness alone.

The present invention enables a relatively rapid reliable test for damage to the nervous system by measuring responses to multiple, simultaneously presented, stimuli, that affect appropriately the response-regulating mechanisms of the nervous system, so that these response-regulating mechanisms do not reduce the responses to the stimuli, with the effect of making the recorded responses more reliable. Another objective of spatially sparse stimuli is to make measurement of spatial interactions that might be of particular utility more practical, by making particular spatial arrangements of stimuli more or less common in the total spatio-temporal signal. The term spatial can also be extended to other stimulus dimensions than the primary temporal dimension, which marks the temporal progress of the time-evolution of the stimulus sequences. For example temporally sparse signals could also be present in a plurality of auditory stimuli along the separate stimulus dimensions of spatial position and frequency of sound vibration. So while frequency of vibration might be regarded as a temporal stimulus dimension it is not the primary temporal dimension along which the plurality of stimulus sequences evolves in-order to estimate an MSER.

Alternatively, the plurality of stimuli might be multi-dimensional, including for example 2 dimensions of space, say elevation and azimuth in the space around a subject, and the frequency of vibration of sound. The dimensions could also correspond to poly-sensory stimulus modalities, for example sound, vision and somato-sensory stimuli. In all cases the temporally sparse stimuli should be arranged to be sparse within the stimulus dimensions other than the primary time dimension, to minimise lateral masking within or across those stimulus dimensions, or be arranged to enhance particular relationships within or across the stimulus dimensions. All these objectives can be met by use of a particular class of stimuli termed spatially sparse stimuli. The prospect of measuring poly-sensory MSERs is anticipated by James A. C. and Maddess (International Application Number: PCT/AUO1/00343). The possibility of measuring interactions between poly-sensory MSERs is anticipated by Maddess T and James A. C. (U.S. Pat. No. 6,315,414). Thus, the present invention is an improvement upon those patents and applications.

In another aspect the invention provides a method for simultaneously assessing the functional status of component parts of the nervous system of a subject, said method comprising:

(a) presenting to one or more parts of the sensory nervous system of the subject stimulus sequences having different temporal modulation sequences of the appropriate stimulus modality for each stimulated part of the sensory nervous system, the stimuli having different sequences for each stimulated part;

(b) fluctuating the temporally modulated stimuli between a null stimulus condition and at least one non-null stimulus condition selected from the group consisting of stimulus conditions contrasting with the null stimulus condition, wherein the probability of encountering the null stimulus condition in the stimulus sequences is higher compared to the probability of encountering one of the non-null stimulus conditions, and wherein the temporally modulated stimuli permit estimation of linear and non-linear weighting functions characterising measured responses to each stimulus presented to each part of the nervous system;

(c) arranging that the non-null stimulus conditions occur with a low probability of having another non-null stimulus appearing at a near neighbour location across the non-temporal stimulus dimensions, or arranging that the non-null stimulus conditions occur with specific neighbour separations across the non-temporal stimulus dimensions to enhance the measurement of particular interactions across those stimulus dimensions;

(d) estimating some or all of the coefficients of the linear and non-linear weighting functions for each stimulus sequence from the measured responses to said stimuli, to isolate separate responses from the separately and simultaneously stimulated component parts of the nervous system.

The non-null stimulus conditions include stimulation of one or more of the senses. In a preferred embodiment of this type, the stimulation is selected from the group consisting of tactile stimuli, olfactory stimuli, thermal stimuli, auditory stimuli or visual stimuli or a combination thereof.

The auditory stimuli may comprise different pressure levels or different tones. The tactile stimuli include any suitable somatosensory stimuli, including different pressure levels and different frequencies of a stimulus pressed against the skin or other tissues. Olfactory stimuli might be selected from a standard set of distinct scents where a valid null stimulus would be air with no scent. The visual stimuli may comprise images of different brightness, whether actual or illusory, different luminance or contrast levels or modulations, different colours or colour contrasts, different patterns, textural densities or types, binocular depths, lighting cues to depth, modulations of the illuminant, different pattern orientations or directions of movement, different image sizes, i.e., any valid modulation of the visual nervous system.

In a preferred embodiment for testing the visual nervous system a portion of a subject's visual field is divided into a plurality of regions where that plurality forms a two-dimensional array across the visual field. The array of stimulus regions would be divided into a tessellation of non-overlapping blocks of 2 by 2 adjacent neighbouring regions. Within each of these blocks of 4 neighbouring regions the top left region is assigned to be of class A, the top right region of class B, the bottom left region of class C, and the bottom right region would be designated of class D. The tessellation would thus divide the whole of the plurality of stimuli in 4 classes of neighbours, with the intent that at any particular time step in the evolution of the plurality of stimuli only one of the four classes could be active in the sense of the regions of that class having a probability, P, of displaying a non-null stimulus, while the regions of the other 3 classes would display a null-stimulus, or have a probability much lower than P of presenting a non-null stimulus. Notice that this spatial arrangement is rendered possible by having temporally sparse stimuli modulate the appearance of the regions by presenting null and non-null stimulus conditions in time. Older binary stimuli do not have this possibility as there are no null-stimuli, and so all stimulus regions must have neighbours that display a non-null stimulus.

Thus, a spatially sparse stimulus would be produced by insuring that the particular temporally sparse sequences employed would be arranged so that if a region of a particular class displayed a non-null stimulus, then all the other three region classes within each 2 by 2 block would display a null stimulus, or have a very low probability of displaying a non-null stimulus. In this way the total stimulus is rendered spatially sparse.

In another preferred embodiment, the two-dimensional array of stimulus regions is divided up into two classes of regions, denoted class A and class B, interleaved like the lack and white squares of a checkerboard. That is, diagonal neighbours are in the same class, but neighbours sharing a boundary are in separate classes. As with the configuration above the stimulus sequences modulating the appearance of the stimulus regions are temporally sparse stimulus sequences containing a null stimulus condition and relatively infrequent occurrences of one or several non-null stimulus condition(s). These temporally sparse stimuli are arranged across the tessellation of stimulus regions of classes A and B so that when the regions of one class, have a possibility of being activated with a non-null stimulus, then the regions of the other class are all null stimuli, or have a much lower probability, of being activated. This arrangement also reduces the number of directly adjacent neighbouring regions that display a non-null stimulus at any time step in the sequence of stimuli and so the stimulus is rendered spatially sparse.

In another preferred embodiment, the array of stimulus regions is hexagonal and it is divided up into adjacent triplets of hexagons wherein like regions within each triplet are designated to be in classes A, B and C. As with the configurations above the stimulus sequences modulating the appearance of the stimulus regions are temporally sparse stimulus sequences containing a null stimulus condition and relatively infrequent occurrences of one or several non-null stimulus condition(s). These temporally sparse stimuli are arranged across the stimulus regions so that regions of one class, A, B or C, have a relatively low probability, P, of being co-activated with a non-null stimulus, while regions of the other two classes has 0 probability, or a probability much lower than P, of being activated. This arrangement reduces the number of neighbouring regions that display a non-null stimulus at any time step in the sequence of stimuli and so the stimulus is rendered spatially sparse. Preferably, the step of presenting (step (a)) comprises:

dividing the visual field of view of each eye into a plurality of stimulus regions so as to roughly isolate confluent streams within the optic nerve, optic radiations and visual cortex due to their retinotopic arrangement and/or to stimulate different parts of areas of the brain concerned with vision; and presenting to either or both eyes stimuli having different temporal modulation of the appearance of each of the regions of the visual field of each eye, the stimuli being different for each of the corresponding regions within the visual field of view of each eye.

Preferably, the visual field is divided into quadrants partitioning the visual field along axes defining at least one member selected from the group consisting of the temporal, nasal, inferior and superior visual fields and concentrically organised partitions of these quadrants, which permits separate stimulation of central and peripheral parts of the visual field.

Preferably, in the above-preferred embodiment, the stimuli include modulation of the brightness or contrast of elements within each of the stimulus regions between two or three brightness levels or between two or three contrast levels.

Suitably, the temporally modulated stimuli and are sufficiently complex so as to permit estimation of some or all of the coefficients of linear and non-linear weighting functions characterising the measured responses to each stimulus presented to each part of the nervous system.

Preferably, the stimulus sequences comprise aperiodic or pseudorandom stimulus sequences that are temporally sparse, thus permitting differing neighbouring regions to display null-stimuli.

Preferably, the linear and non-linear weighting functions are Wiener or Volterra kernels.

Suitably, the latency to selected peaks within time course of linear kernels and/or the shape of the kernels and/or their amplitudes are used as measures of the functional status of component parts of the nervous system.

The non-null stimulus conditions within a stimulus sequence preferably occur with an average frequency of between about 0.25 and about 20 per second per stimulus region, more preferably between about 1 and about 6 per second per stimulus region. In an example of video stimulation at a frame rate of 50 Hertz this gives a probability of encountering the non-null stimulus within a given stimulus region of between about ½ and about 1/50. The null and non-null stimuli should be arranged across the non-temporal dimensions of the totality of stimuli such that any non-null stimulus has a low probability of having a near neighbour that is simultaneously also in a non-null stimulus state.

In another aspect, the invention provides an apparatus for assessing the functional status of component parts of the nervous system, comprising:

stimulation means for presenting to the sensory nervous system of a test subject stimulus sequences having different temporal modulation sequences of the appropriate stimulus modality for each stimulated part of the sensory nervous system, the stimuli having different sequences for each stimulated part that are spatially sparse across the non-time dimensions of the sensory dimensions stimulated;

monitoring means for monitoring responses to said stimulus sequences in said test subject; and processing means for determining coefficients of linear and non-linear weighting functions for each stimulus sequence from the measured responses to said stimuli.

In the case of testing visual function exclusively the stimulation means suitably comprises means for presenting a stream of separate, viewing images presented to either eye or both eyes.

Suitably, the different viewing images comprise images of different image contrast levels.

The monitoring means preferably comprises recording means for recording responses to said stimulus sequences in said test subject.

Preferably, the recording means record visual evoked potentials to provide an objective indication of the said responses.

The processing means suitably includes timing means and means for receiving signals from the recording means indicative of said response.

The invention may also be said to consist in any alternative combination of the features that are indicated in this specification. All equivalents of these features are to be considered as included whether or not they are explicitly mentioned.

LIST OF FIGURES

Figure 2:
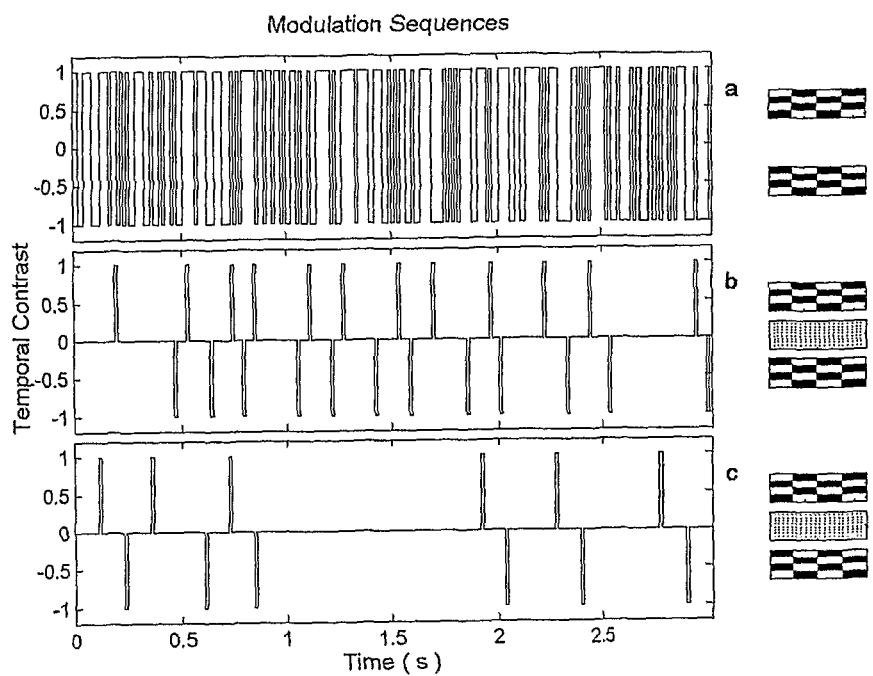
Figure 3:
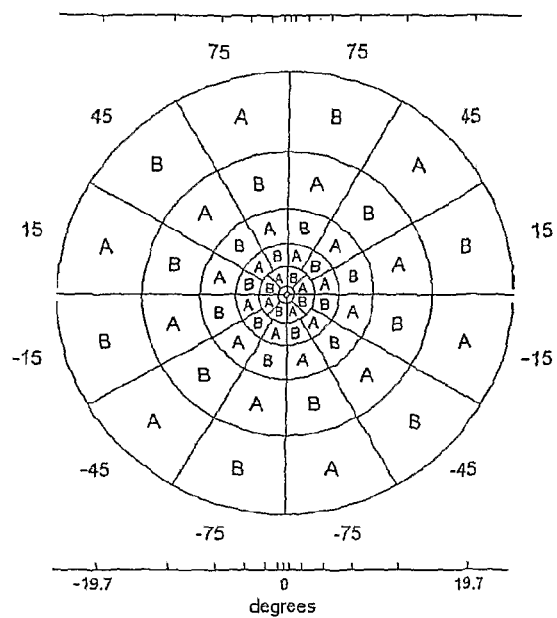
Figure 3:
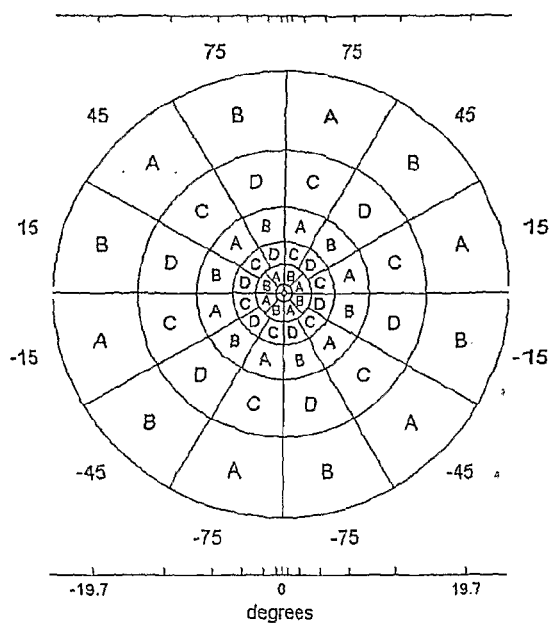
Figure 4:
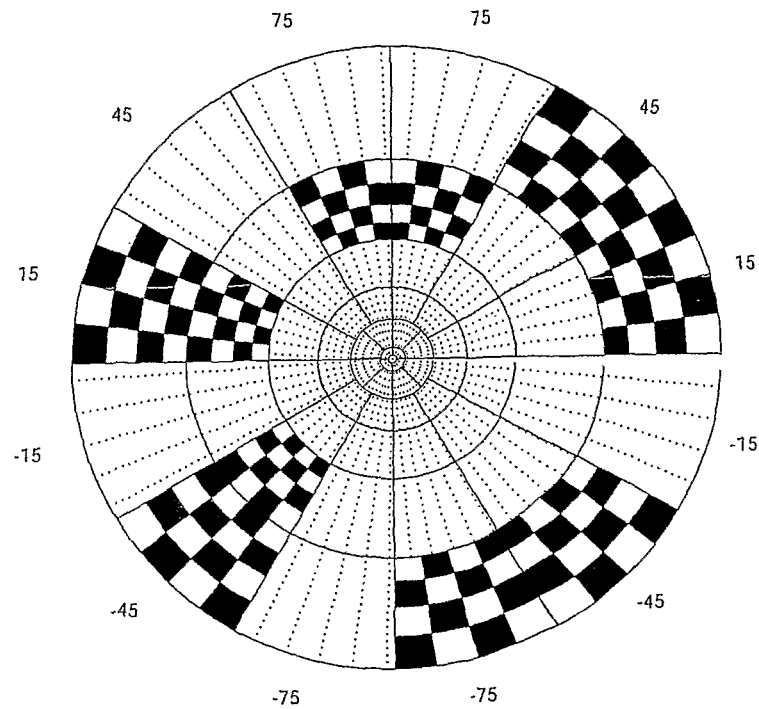
Figure 5:
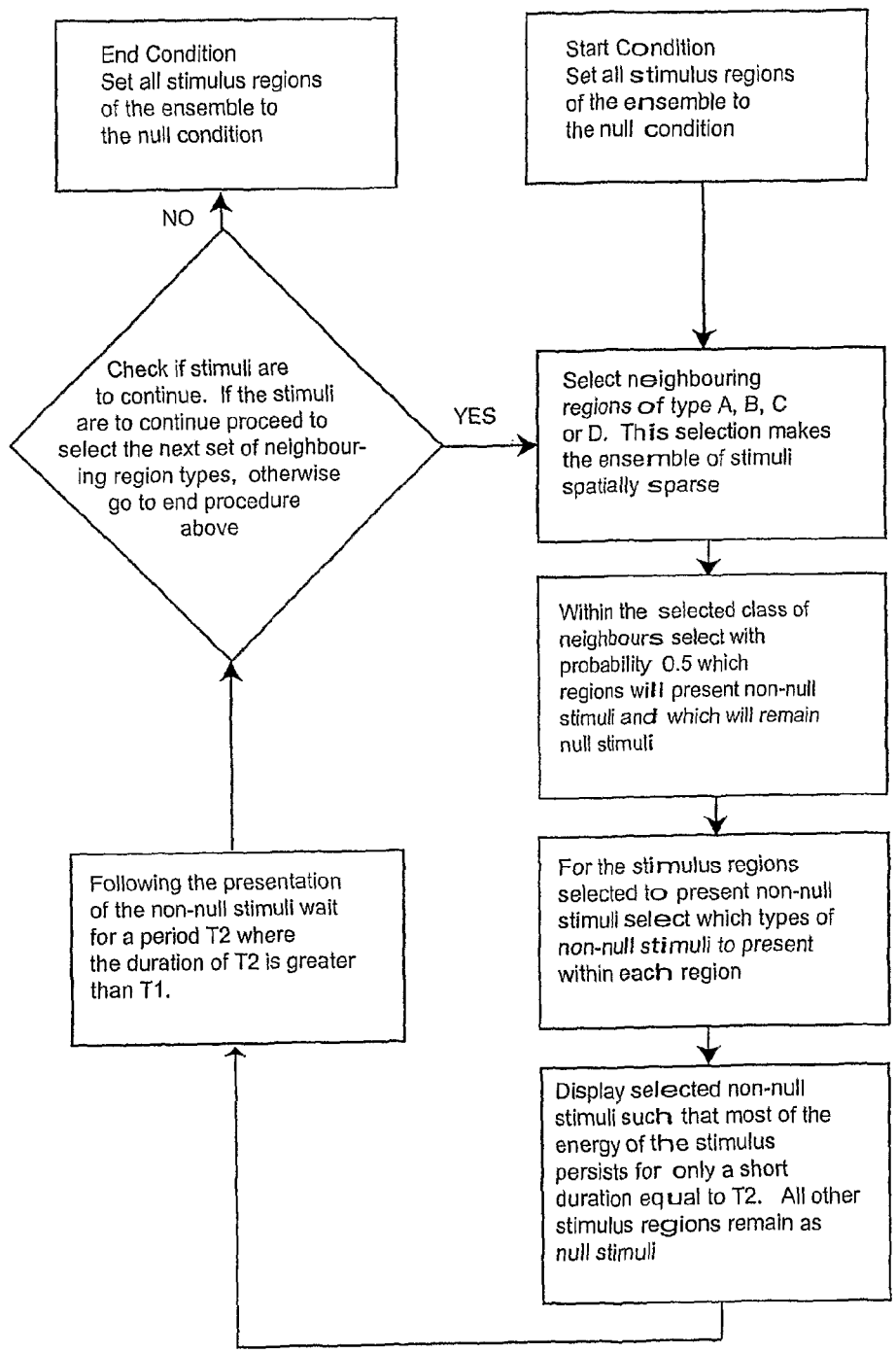
Figure 6:
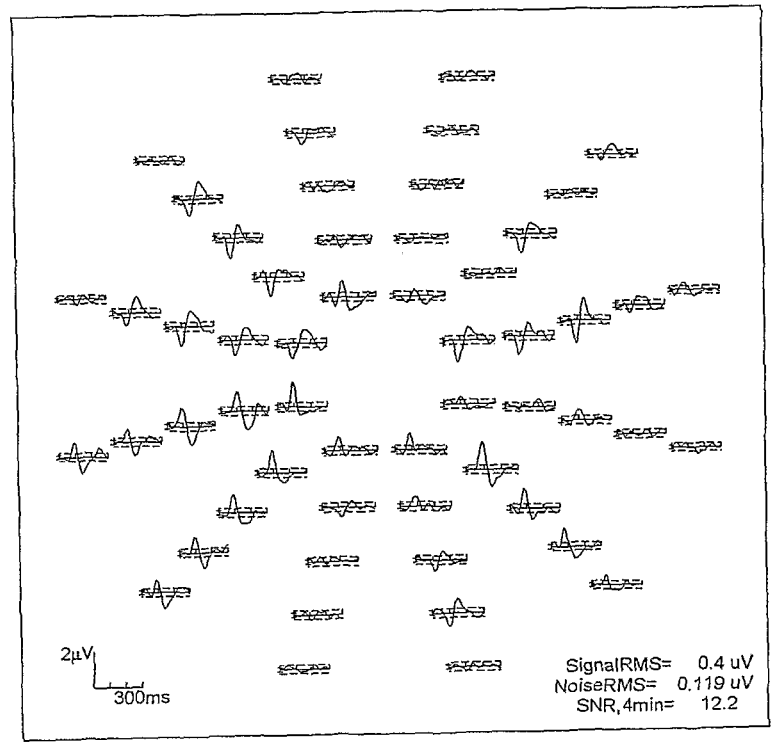

Preferred embodiments of the invention will be described with respect to the accompanying drawings, of which:

FIG. 1 is schematic diagram indicating components of a system for assessment of neural function, FIG. 2 gives examples of stimulus sequences that might be used in the system of FIG. 1, FIG. 3 are patterns indicating how the stimuli may be presented the eye in assessment of a visual sensory system where the symbols A to D represent classes of neighbours within the stimulus ensemble, FIG. 4 is an instance of a temporally sparse stimuli using sequences as in FIG. 2, but where the non-null checkerboard stimuli are not spatially sparse, as some near neighbours are co-active, FIG. 5 is a flowchart showing how a sequence of stimuli may be created for the system in FIG. 1 using a system of neighbouring regions as exemplified by the diagrams of FIGS. 2 and 3, FIG. 6 gives examples of responses to ensembles of stimulus sequences with there being one response per region such as shown in FIGS. 3 and 4

Figure 7:
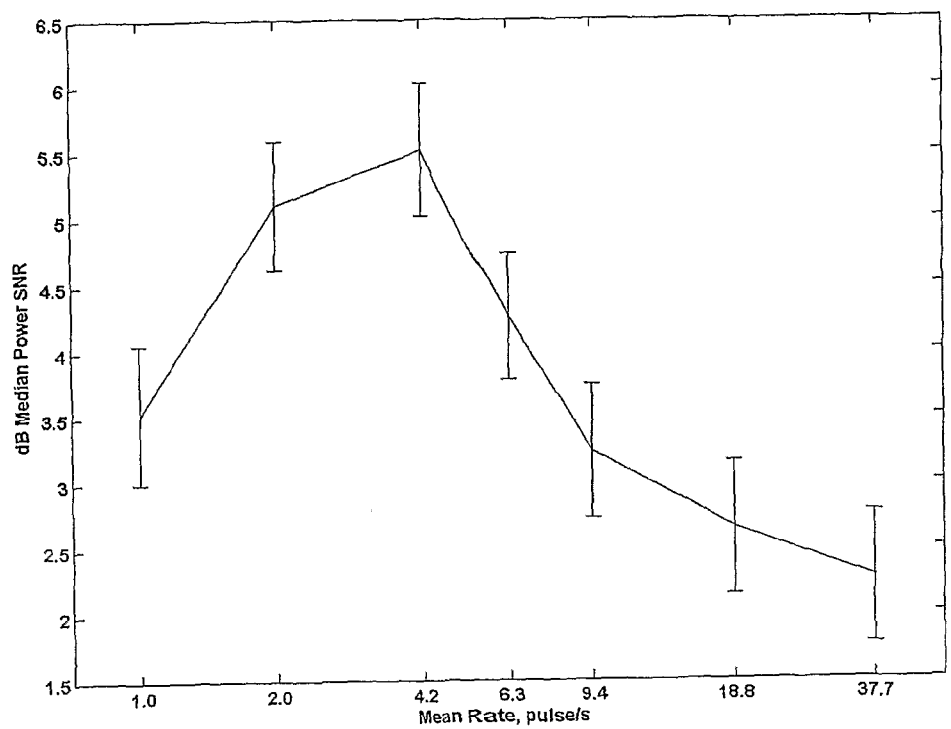
Figure 8:
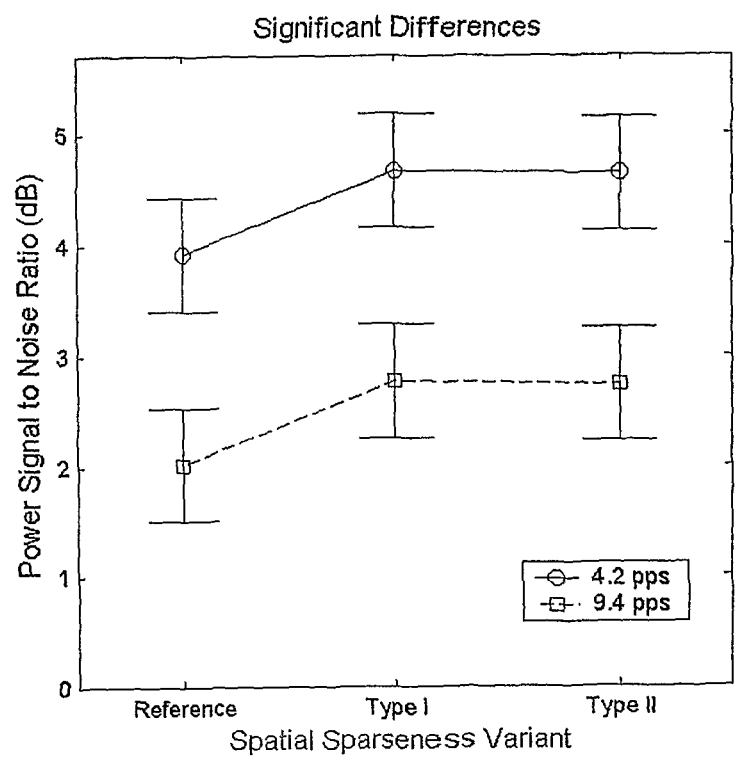
Figure 9:
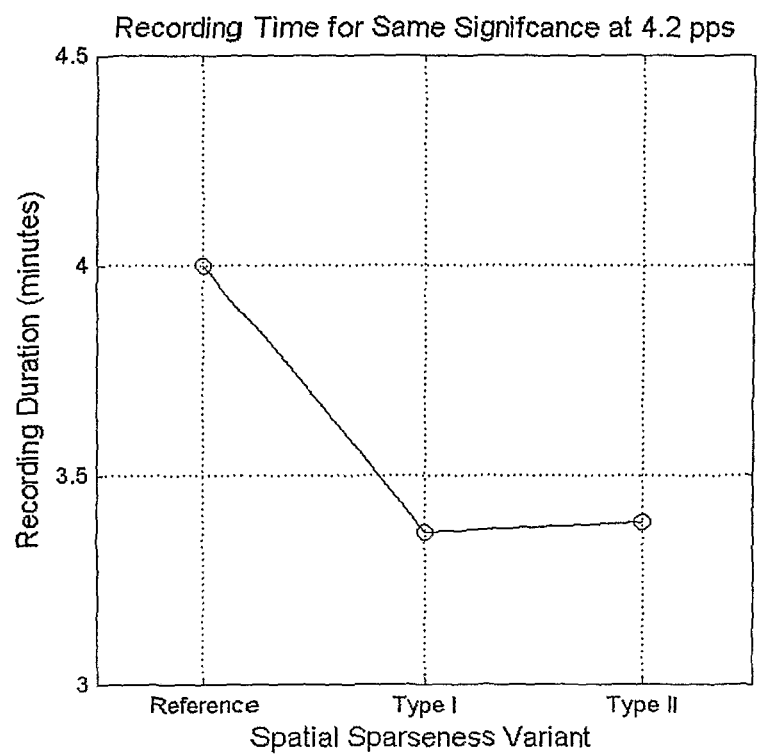
Figure 10:
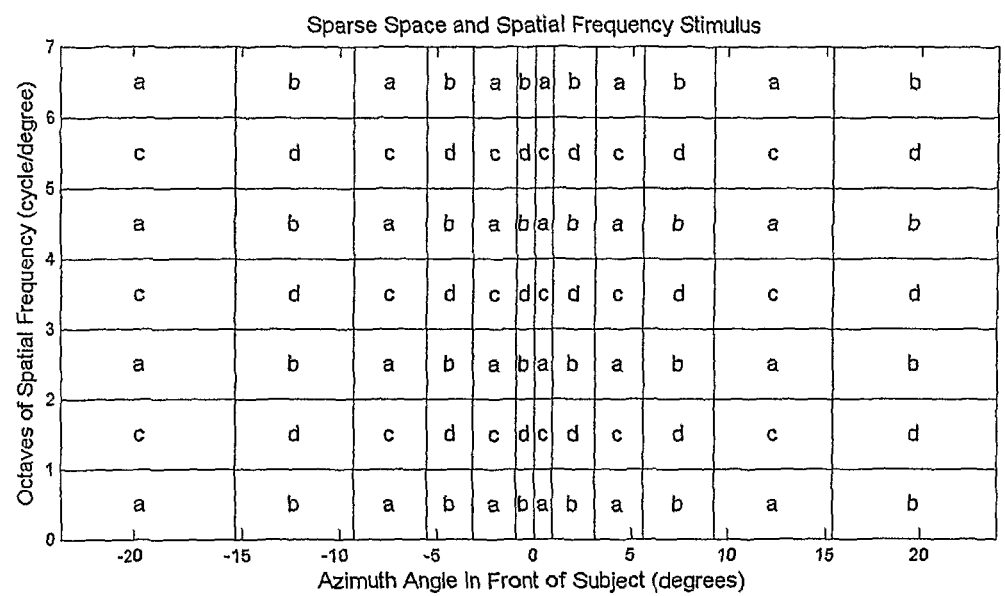
Figure 11:
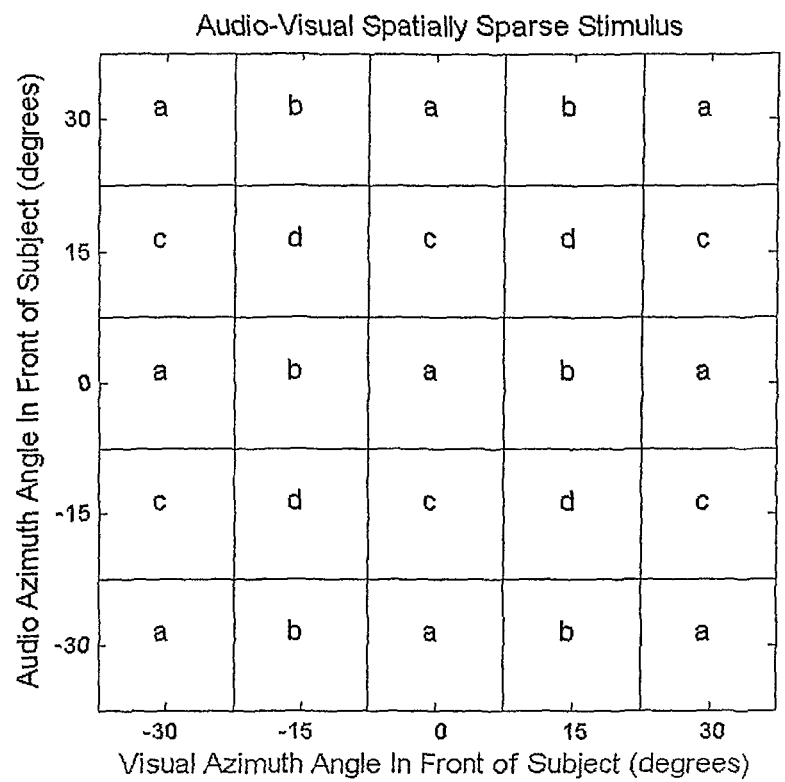
Figure 12:
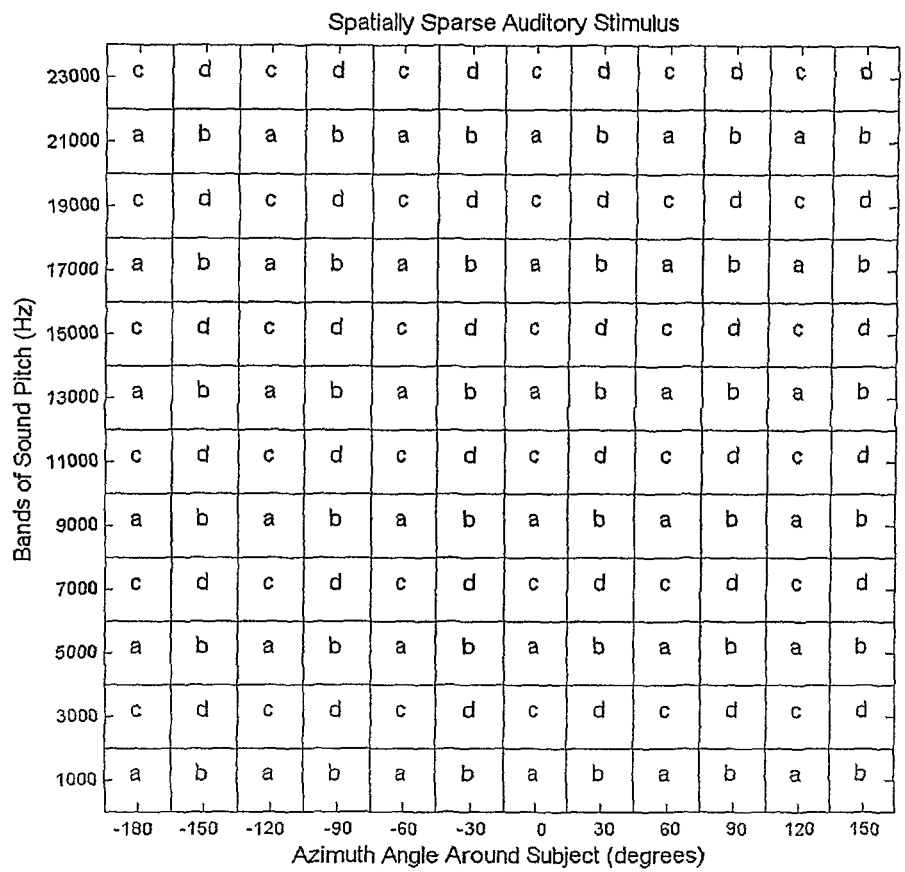
Figure 13:
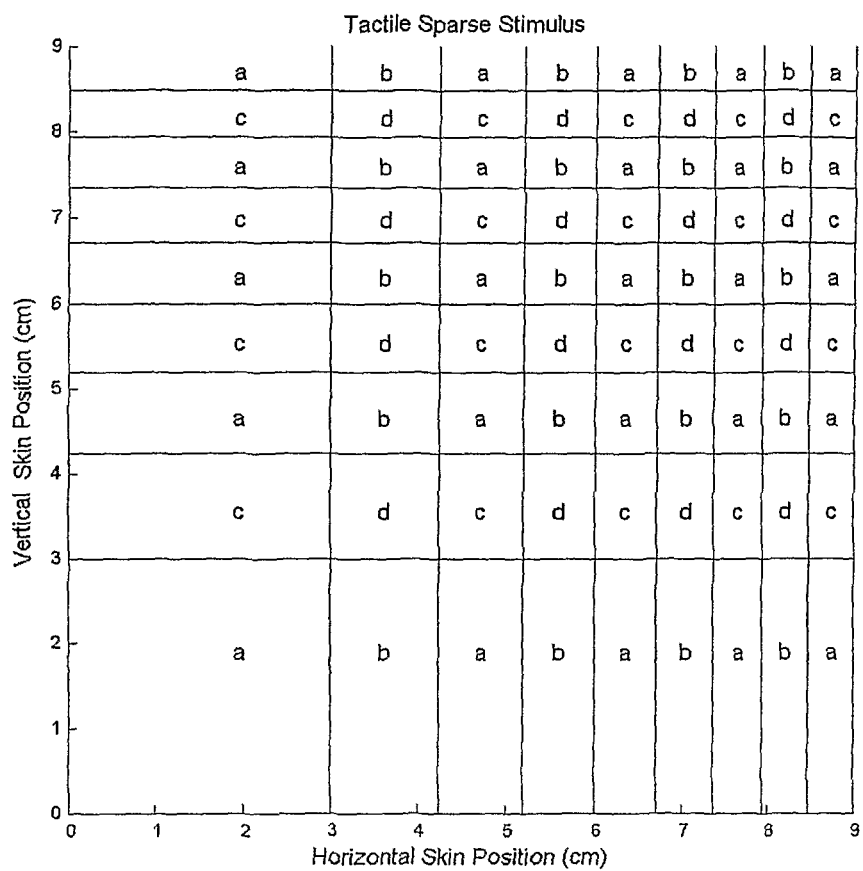

FIG. 7 is a graph indicating the effect of the rate of presentation of non-null stimuli on the Signal to Noise Ratio (SNR) of the responses, FIG. 8 is a graph comparing the effect on SNR of spatially sparse and temporally sparse stimuli, FIG. 9 is a graph indicating how spatially sparse stimuli can improve the time required in measuring responses to achieve the same level of accuracy, FIG. 10 is a pattern indicating how spatially sparse stimuli may be presented with a third spatial dimension which concerns the spatial frequency content of the test patterns presented as in FIG. 4, FIG. 11 is a pattern illustrating how other stimulus dimensions may be involved with presentation of spatially sparse stimuli here illustrating a spatial dimension for the azimithal position of sound sources co-localised with visual stimuli, FIG. 12 is another pattern illustrating how other stimulus dimensions such as sound pitch may be involved with presentation of spatially sparse stimuli, and FIG. 13 is a pattern illustrating spatially sparse stimuli presented in spatial dimensions of tactile.

DETAILED DESCRIPTION OF THE PREFERRED EMBODIMENTS

Referring to the drawings it will be appreciated the invention can be implemented in a variety of ways for a variety of purposes. The description here is by way of example only.

FIG. 1 is a functional block diagram of the basic system components forming a non-limiting embodiment of the apparatus of the invention for assessing the functional status of component parts of the nervous system. The solid arrows indicate features such as the idealised subject, or the connection point of the electrodes to the back of the subject's head. The open arrows indicate the flow of information and processing within the device. Thus, in the case of visual stimulation a graphics control unit generates the spatially sparse stimuli and presents them on the visual display unit. The subject observes the presented stimulus sequence while the amplifier detects the electrical brain responses evoked by the stimuli and passes them on for recording and estimation of the linear and or nonlinear response functions by the kernel estimation unit.

FIG. 2 illustrates three types of pseudorandom temporal stimulus sequences. These sequences represent the modulation of one stimulus region in an ensemble of stimuli as exemplified by FIGS. 3, 4. The upper panel (a) illustrates a binary sequence where the stimulus varies between two conditions, −1 and 1. There are two possible non-null stimuli, representing the −1 and the 1 states, which are presented in the two small inserts to the right of the temporal trace. The 1 and −1 conditions are both valid stimuli, which happen to be contrast, reversed versions of a small checkerboard pattern. The central panel (b) illustrates a ternary, or bipolar, version of a sparse pseudorandom stimulus sequence. In this instance, the stimulus has three conditions: a more frequent null stimulus condition, the 0 stimulus condition, and two less frequent non-null stimulus conditions, at levels above and below the null stimulus condition, levels −1 and 1, as in (a). Again the small inserts to the right indicate possible instantiations of such stimuli, where the stimuli representing the −1 and 1 conditions are as in the upper trace, and the null stimulus is a blank featureless region of the same size. Here the neutral grey of this featureless null stimulus is represented by a stippling of small dots. In (b) The mean rate of presentation of non-null stimuli, levels −1 and 1, is 9.4 presentations per second. The lowest panel, (c) illustrates a more temporally sparse ternary pseudorandom stimulus sequence having a mean rate of presentation of non-null stimuli, conditions −1 and 1, at 4.2 presentations, or pulses, per second.

FIG. 3 shows schematic representations of the spatial layout of the visual stimulus used in non-limiting embodiments of the apparatus of the invention providing spatially sparse stimulation. The upper panel shows the case where a contiguous array of regions is parsed into two classes of neighbouring regions labelled A and B. The lines mark the borders of the stimulus regions and were not visible on the stimulus device. The array of stimulus regions is rectangular in polar coordinates, giving them the appearance of a dartboard. Spatial layouts similar to this are preferred when recording evoked responses based mainly upon the activity of the striate visual cortex, which receives the bulk of the input to the visual cortex from the eyes, but where the input from the eye is not uniform. The dartboard array tends to reverse the effect of this non-uniform input from eyes such that, providing the array of stimulus regions in the array remains centred on the projection of the fovea of the eye into visual space during the test, then each region stimulates approximately equal areas of the striate visual cortex. In this embodiment the temporally sparse stimuli are arranged so that when regions of type A have a relatively low probability, P, of displaying a non-null stimulus, the regions of type B have a probability of 0 of showing a non-null stimulus, i.e. they will present null stimuli, when regions labelled A have some probability of displaying a non-null stimulus. At a later time in the stimulus sequence the roles of regions labelled B and A would exchange. Thus, regions of type A or B tend to have relatively few neighbours that simultaneously display a non-null stimulus and so the totality of the stimuli is spatially sparse at every time. This spatial arrangement is called Type I. In the Type I stimulus variant no region ever has neighbours sharing an extended border that concurrently present a non-null stimulus. Neighbours that share a corner within the array can simultaneously present non-null stimuli. The lower panel shows the same array of stimulus regions but where the stimulus regions are now divided into 4 neighbour types: A, B, C, and D. This type of spatially sparse stimulus is referred to as Type II. A diagram of the flow of stimuli in this particular non-limiting embodiment is shown in FIG. 5. In Type II the temporally sparse stimuli are arranged so that each of the 4 subgroups of regions has a time when its group has a relatively, low probability, P, of displaying a non-null stimulus. At that time the other 3 types of regions have a probability of 0, of showing a non-null stimulus, i.e. they will present null stimuli. On a subsequent time steps of the stimulus sequence the roles of regions labelled A to D would exchange in some order so the totality of the stimuli is spatially sparse at every time. Notice that for the Type II stimulus variant no first order neighbours, either those sharing contiguous borders, or those sharing corners, ever simultaneously presents a non-null stimulus and hence the totality of stimuli across the ensemble are spatially sparse.

FIG. 4 shows a FIG. 3 where various regions illustrate the null and non-null stimuli used in a particular embodiment for testing the visual field. Notice that several pairs of regions each are filled with a 4 by 4 pattern of checks. Like the whole array of stimuli the checks are rectangular in polar coordinates. In the actual stimulus the black checks had a luminance of 2 candelas per meter squared, and the white checks had a luminance of 92 candelas per meter squared. Notice that two types of non-null stimuli are present, where the black and white checks are exchanged, or contrast reversed, as shown in FIG. 2. For the null stimuli a given region was a featureless grey at the mean luminance, which is represented by level 0 in FIG. 2b,c and in this figure by regions marked by a stippling of small dots. The presentation of one checkerboard type is indicated by a 1 in FIG. 2, and the presentation of a reverse contrast checkerboard is indicated by a −1 in FIG. 2. For example the pair of regions in the outermost ring of the stimulus centred on the right −45 and −75 degree positions are contrast reversed with respect to each other, as are the pair of regions found on the left −45 spoke, and the pair of regions in the second ring fro the outside centred on the left and right 15 degree spokes. The each member of the other pairs of regions display the same polarities of checkerboard and so are not contrast reversed with respect to each other. The two polarities of checks were used with equal probability in all the temporally sparse sequences to insure that over time the average brightness at all regions was equal to the mean luminance of 45 candelas per meter squared.

FIG. 5 is a flowchart illustrating the processes of the non-limiting design of the temporal evolution of the Type II spatially sparse stimulus ensemble of FIG. 3. Initially all stimulus regions are set to the null stimulus condition. The flowchart shows that some time later one of the 4 types of neighbours, type A, B, C, or D is selected and half of those are chosen at random to display a non-null stimulus. Of those selected stimuli, let us say type A, they are further selected to show different non-null stimuli. In the non-limiting example described in FIG. 7 there were two equally likely non-null stimuli corresponding to the positive and negative contrasts of the checkerboard patterns as illustrated in FIGS. 2 and 4. The selected stimuli are then presented for a short time, $T_1$. In the non-limiting example of FIG. 7 the stimuli persisted for 13.3 ms, but as described in the flowchart only the major portion of the effective energy of the stimuli need be briefly presented. Following the presentation of non-null stimuli in the selected regions the regions are returned to the null stimulus state. Following a relatively long period, $T_2$ ($T_2 > T_1$), the process returns to the neighbour selection process again, unless the temporal sequence has ended. In the non-limiting example of FIG. 7 the neighbour selection process cycled through the neighbours types of FIG. 3, Type II, in the order A, B, C, D, A, B, C, . . . and so on but in practice the neighbour selection process could be randomised providing the number of times each type was shown in the total stimulus sequence was balanced. In either case no stimulus region within the ensemble would have a neighbour that was simultaneously active and so the ensemble of stimuli is rendered spatially sparse across the dimensions of the stimulus ensemble that do not correspond to the temporal evolution of the individual stimuli.

FIG. 6 gives examples of responses to each of the ensemble of independent stimulus sequences applied in a spatial layout like those of FIGS. 3 and 4. Polar angle corresponds to stimulus layout, eccentricity is linearized compared to actual stimulus, which was log-spaced. There is thus one response waveform for each stimulus region. Stimulus sequence had mean rate of presentation 4.2 pulses/s per region as in FIG. 2c, and the pulsed non-null stimuli were two video frames long (26 ms), and alternated in polarity within each region. The because the stimulus sequences a statistically independent responses, linear or nonlinear weighting functions, can be estimated for each region even though only a single aggregate response from the nervous system might be monitored. In this non-limiting example a recording of the visual evoked potential differentially measured from one pair of electrodes on the scalp of the occipital pole of the skull as illustrated in FIG. 1. The responses can be estimated by means such as cross-correlation or regression of the responses against the stimuli, the former was used here. The responses are thus estimates of the response to a single presentation of a stimulus at each region. Error bars at time zero indicate +/−1 standard error, the dashed lines indicate +/−2 standard errors, giving an approximate pointwise 95% confidence interval, uncorrected for multiple comparisons. Data was obtained from 4 runs of 55 seconds from one subject. The scale bars at bottom left give the voltage and time scale for the responses. The median (across regions) RMS signal, Noise and Signal to Noise Ratio (SNR), scaled for a 4 min stimulus, are given in the inset at bottom right.

FIG. 7 presents data from 25 subjects showing the independent effect of presentation rate of non-null stimuli upon the median power signal to noise ratio (SNR) +/− one standard error. The power signal to noise ratio is expressed in decibels (db). The median power SNR was computed across the SNRs for each stimulus region and presentation rate. The stimulus regions had a spatial layout as illustrated in FIGS. 3 and 4. In this non-limiting example the stimulus was displayed on a monitor that had a vertical refresh rate of 75 frames per second. The fastest stimulus, 37.7 pulses/s shown at right, was a contrast-reversing stimulus, that is having no interleaved null stimuli, having a temporal evolution as shown in FIG. 2a. The next fastest stimulus, 18.8 pulses/s was also contrast reversing but where each stimulus persisted for 2 frames of the stimulus sequence (26 ms). The stimuli having slower presentation rates were temporally sparse, having null stimuli interspersed between the non-null stimuli as in FIGS. 2c,d, where the non-null stimuli persisted for two video frames. In this case no attention was given to the spatial sparseness of any of the stimuli. The improvement in SNR from contrast reversing, 37.7 pulses/s to the apparent optimum sparse rate, 4.2 pulses/s is around 3 dB, corresponding to a doubling of power SNR, which means a criterion SNR can be obtained in one half the recording time by the sparser 4.2 pulses/s stimulus. The temporal evolutions of a single region of the temporally sparse 4.2 pulse/s and 9.4 pulses/s stimuli are illustrated in FIGS. 2b,c.

FIG. 8 is an illustration of the advantage of spatially sparse stimuli over purely temporally sparse stimuli. The figure represents the output of a multiple regression model applied to the median power SNR data of 10 subjects. As in FIG. 5 the SNRs are the medians across the stimulus ensemble. Each subject was tested with 6 temporally sparse stimuli. The two reference conditions were temporally sparse stimuli presented at 4.2 and 9.4 pulses/s as illustrated in FIG. 2c,d. The spatial relationships between the neighbours of the reference stimuli was randomised, hence there was a reasonable chance of two neighbours simultaneously displaying a non-null stimulus. FIG. 4 gives an example of a possible frame of this stimulus ensemble. Thus, the reference stimuli were only poorly spatially sparse. The reference stimuli were thus similar to those used to derive FIG. 7. The four remaining stimuli used the Type I and Type II spatially sparse stimulus conditions of FIG. 3 in conjunction with the same mean presentation rates of 4.2 and 9.4 pulses/s. For both rates the spatially sparse stimuli gave significant ($p<0.05$) improvements in median power signal to noise ratio (SNR) compared to their corresponding reference stimulus. The difference between the SNRs obtained for the two presentation rates was also significant ($p<0.001$).

FIG. 9 shows how the improvements in median decibel power SNR shown in FIG. 8 can be translated into the time required to generate a signal having the same SNR for different levels of spatial sparseness. In the experiments summarised by FIGS. 6, 7 and 8 the total recording time was about 4 min. per test condition. The points shown are computed from the 4.2 pulse/s data of FIG. 8. The points demonstrate that to match the SNRs produced by a 4 min reference stimulus the Type I and 2 spatially sparse stimuli would require 16% less time. This is not as large an effect as shown in FIG. 7, for changing the rate of presentation from 37.7 to 4.2 pulses/s, but it is nevertheless a substantial improvement over conventional temporally sparse stimuli.

FIG. 10 is an illustration of a non-limiting variant of the spatially sparse Type II stimulus of FIG. 3 where a $3^{rd}$ spatial dimension is added. The added dimension is the spatial frequency content of the visual stimuli presented within in each region of FIG. 3. Thus, at any particular time a given region of FIG. 3 can display a pattern dominated by one of 7 spatial frequencies where each of the 7 spatial frequencies is separated by one octave. This separation insures that largely exclusive populations of neurons within visual area one of the human are stimulated. Insuring that only stimuli separated by one octave apart are ever co-active thus renders the stimulus sparse along the spatial frequency dimension. The abscissa is similar to the scaling along the horizontal meridian of the stimuli illustrated in FIG. 3. Note that the symbols a, b, c and d do not directly correspond to those of FIG. 3, but rather indicate the sub-groups of potentially co-active stimuli along the stimulus dimension of visual field azimuth and spatial frequency.

Based on the work of Blakemore C., Nachmias J., and Sutton P., entitled "The perceived spatial frequency shift: evidence for frequency-selective neurons in the human rain", published in the Journal of Physiology, Volume 70, 1970, pages 727 to 750; and the work of Maddess T. and Kulikowski J. J. entitled "Apparent fineness of stationary compound gratings" published in Vision Research, Volume 39, 1999, pages 3404 to 3416; one would expect that a third spatial dimension could be added to the arrangement shown in FIG. 3 where stimuli could be rendered spatially sparse across the resulting 3 spatial dimensions that would produce benefits for testing the visual system. That third dimension would be bands of spatial frequency. Thus, the non-null stimuli could encompass spatial frequency content that differed over several octaves. According to those authors keeping non-null separated in spatial frequency by two or more octaves reduces inhibition between the neural channels processing those stimuli minimizing lateral suppression of response along the spatial frequency dimension. FIG. 10 illustrates a 2 dimensional slice through such a sparse stimulus ensemble where the abscissa corresponds to the horizontal meridian of the patterns of FIG. 3.

FIG. 11 illustrates the extension of the principle of spatially sparse stimuli to other stimulus dimensions that do not correspond to the temporal evolution of the stimuli. Here the stimulus dimension corresponding to the abscissa is azimuth angle in the space seen by a test subject in front them. Negative angles represent angles to the left of the subject, positive angles representing directions to the right of the subject. Zeros degrees thus indicates the direction directly ahead of the test subject. The visual stimuli might be 5 regions that can present null and non-null stimuli at the 5 locations along the horizontal meridian, or at some other elevation angle. The stimulus ensemble also includes 5 auditory stimuli such as clicks. There can either be actual sound sources centred on the visual stimuli or sound sources that are made to appear to emanate from those visual stimuli by presenting them with a temporal disparity and or a sound pressure difference between the two ears such that the sounds appear to emanate from centres of the 5 visual stimuli. Thus the ordinate has the same physical units as the abscissa, but corresponds to the apparent direction to the source of the auditory stimuli. The letters a to d indicate that the stimuli are to be sparsely presented within this two dimensional audio-visual domain such that no neighbour within the ensemble has a large chance of being co-activated.

FIG. 12 illustrates a second example of the extension of the principle of spatially sparse stimuli to other stimulus dimensions that do not correspond to the temporal evolution of the stimuli. Here both stimulus dimensions are related to sound qualities. The abscissa is similar to that of the ordinate of FIG. 11 and corresponds to the directions to the centres of apparent or actual sound source locations emanating from at positions all around a subject in a horizontal plane. The ordinate here is sound pitch, where high frequencies of sound pressure variation corresponded in the usual way to high-pitched tones. Thus, the ensemble of stimuli have a range of source locations and dominant pitches. The letters a to d indicate that the stimuli are to be sparsely presented within this two dimensional auditory-domain such that no neighbour has a large chance of being co-activated. The stimuli could be combined with visual stimuli presented at the same locations as the sound sources, providing they were also presented in a sparse fashion similar to FIG. 7. Note that human pitch discrimination is very good so the dominant tones can be quite close in frequency and still active quite different population of sensory neurons within the auditory system.

FIG. 13 illustrates the principle of spatially sparse stimuli presented in spatial dimensions of tactile space. The regions of the diagram represent regions of the skin to be stimulated by pressure or temperature stimuli. The scaling of the regions is designed to mimic the changing density of neural sensory apparatus across the skin such that each stimulus region stimulates an approximately similar population of sensory elements. This is similar to the logic of FIGS. 3 and 4 where the stimulus region size is designed to stimulate similar sized populations of neurons within the striate visual cortex. The letters a to d indicate that the stimuli are to be sparsely presented across this two dimensional tactile-domain such that no neighbour has a large chance of being co-activated.

A stimulus ensemble using combinations of stimulus dimensions shown in FIGS. 10 to 13 would also be possible.

It has been discovered that parts of the nervous system are controlled by mechanisms regulating their sensitivity and that some of these systems increase the response of the neurones they are regulating when stimuli appear in relative isolation in non-temporal dimensions of the stimulus, compared to the case when many near neighbours appear simultaneously. This effect, known as lateral masking, was known for visual stimuli present for relatively long presentation times such as occurs in reading crowded letters on a page of text. In this respect, the present inventors have found surprisingly, even for presentation times as short as $1/75^{th}$ of a second, or even if the neighbouring stimuli only have a limited probability of appearing due to pseudorandom presentation of stimuli, that if stimuli are presented with relatively few near neighbours responses are increased compared to the case of having many neighbouring stimuli. Such pseudorandom stimuli are herein defined to be spatially sparse. The enhancing effect of having relatively few pseudo-randomly occurring neighbouring stimuli was true even when the temporal functions governing the temporal appearance of a stimulus in the adjacent regions meant that the chance of many neighbours co-occurring was relatively low. The increased response amplitudes due to spatially sparse stimulation ensure more reliably recorded responses than are obtained with non-sparse stimuli. This was shown by characterising the significant increase in signal to noise ratios obtained to spatially sparse stimuli, compared to reference stimuli having the same mean rates of presentation within each region but where no consideration of the condition of neighbouring stimuli was made. Accordingly, the use of spatially sparse stimulus sequences provides more reliable assessment of neural systems that are subject to response regulation mechanisms of the type described above. More generally, assessment of neural function will be enhanced further by the accurate measurement of the time evolution of neural responses afforded by this invention.

The inventors have reduced their discoveries to practice in a method and apparatus for simultaneously assessing the functional status of component parts of the nervous system as described more fully hereinafter. Briefly, the method involves measuring some or all of the coefficients of linear and non-linear temporal weighting functions known as kernels that characterise the linear and non-linear stimulus evoked responses of component parts of the nervous system. The method employs particular stimulus sequences that not only have a temporal structure that is sufficiently complex to permit calculation of the requisite kernels, but that also have properties causing response regulation mechanisms within the nervous system to generate larger and more reliable neural responses, namely spatial sparseness.

While the method can be applied to stimulation of any sensory modality, such as tactile or auditory stimuli to isolate responses from regions of the nervous system where these different sensory modalities are encoded, the visual stimulation is preferred. This is because of the large number of neurones in the visual pathway and the relative case with which these many neurones can be stimulated by the presentation of images to the eye. As ell, the visual system produces observable stimulus evoked responses in the form of the pupil size and oculomotor activity.

Not wishing to be bound by any one particular theory, the reasoning that led to the development of the present invention is provided below.

As noted above Multi-stimulus Evoked Responses (MSERs) would likely be enhanced if the stimuli used would cause neural response regulation mechanisms to enhance the reliability of the responses recorded. Of possible relevance to assessing multiple regions of the visual field by MSERs is the effect frequently referred to as lateral masking. Assessing multiple regions of the visual field by MSERs most typically includes assessing great portions of the peripheral visual field. Early studies showed that stimuli that were presented to the peripheral visual field were harder to recognise when they were presented with several near neighbours. For example Bouma H. in a paper entitled "Interaction effects in parafoveal letter recognition", (1970, Nature volume 226, pages 177 to 178) demonstrated that, when presented in the peripheral visual field, the central letter in a string of letters is harder to identify than when the same letter is presented alone. That effect is sometimes called letter-crowding. Similarly the presentation of many neighbouring line segments around a test line segment reduces the ability of subjects to recognise the orientation of the test line as reported by Andre-issen J. J. and Bouma H. in a paper entitled "Eccentric vision: adverse interactions between line segments (1976, Vision Research, volume 16, pages 71 to 78). The same authors reported in that paper that the amount of image contrast required to recognise the test line was larger when neighbours were present. The fact that more contrast was required when neighbours were present suggested that a neural regulation mechanism was reducing the visibility of the test line when neighbours were present. Those authors repeated their experiments at various retinal eccentricities, that is at a range of distances in the peripheral visual field, and found that the amount of contrast required to identify the test line doubled for neighbours that were within about 0.25 of the angle drawn between the peripheral test location and the point of fixation, the point of fixation being the projection into visual space of the fovea. In those experiments the line segments were presented for 100 ms and 8 neighbours were presented simultaneously. Like letters on a page of text, the line segments of those authors were broadband in spatial frequency. Their results have recently been confirmed for narrow-band Gabor wave-packet stimuli by Wilkinson F., Wilson H. R., and Ellemberg D. in a paper entitled "Lateral interactions in peripherally viewed texture arrays" (1997, Journal of the Optical Society of America, volume A14, pages 2057 to 2068) where 10 neighbouring wave-packets were presented for a duration of 100 ms. The basic effect of the visibility of Gabor wave-packet stimuli being reduced was demonstrated for relatively central vision where up to 56 neighbours were presented for 40 ms at locations between 0 and 18 degrees from fixation.

These crowding effects are of interest in disorders affecting the visual cortex such as amblyopia and reading dyslexia. In both disorders subjects frequently report abnormally strong crowding effects wherein words constructed of close-packed high contrast letters are more difficult to read for persons with these disorders as exemplified by the work on amblyopic subjects presented in a paper by Giaschi D. E., Regan D., Kraft S. P. and Korthe A. C. entitled "Crowding and contrast in amblyopia" (1993, Optometry and Vision Science, volume 70, pages 192 to 197), and on persons with reading dyslexia by the paper by Spinelli D. De Luca M., Judica A. and Zoc-colotti P. entitled "Crowding effects on word identification in developmental dyslexia", (2002, Cortex, volume 38, pages 179 to 200).

All of the above studies are psychophysical ones and therefore on the basis of that evidence alone it would be possible that the lateral masking and crowding effects described are restricted to some higher brain centre, however, the recent paper published by Zenger-Landolt B. and Heeger D. entitled "Response suppression in V1 agrees with psychophysics of surround masking", (2003, The Journal of Neuroscience, volume 23, pages 6884 to 6893) suggests considerable lateral masking occurs in early visual processing. Those authors used functional magnetic resonance imaging to show that lateral masking is characterised by reductions in brain activity in striate visual cortex, a brain area also referred to as visual area 1 or V1. V1 is the region of the cerebral cortex that is the principal receiver of input from the optic nerve, and so too the eye, and is located close to the occipital pole of the brain, that is just beneath the skull near the back of the head above the neck. V1 is also the largest visual area of the cerebral cortex. These properties make V1 ideal for recording MSERs, particularly when looking at diseases that affect the eye, such as glaucoma, or the optic nerve such as multiple sclerosis. Thus, not only is V1 the cortical area most directly related to the function of the eye, but its location at the back of the skull makes it accessible to a variety of monitoring means, such as electrical or magnetic evoked responses or infrared, or T-ray, monitoring. Thus, if a particular stimulus arrangement could minimise the effects of lateral masking then one would expect MSERs recorded from V1 to be enhanced. The results on lateral masking suggest that at least when the number of neighbours is quite large and the presentation time is quite long, at least 40 ms, that larger responses would be recorded if fewer neighbours were present at any one time during the stimulus sequences presented for the measurement of MSERs.

Alternatively, some stimulus arrangement might be able to better characterise effects related to letter crowding in amblyopia and dyslexia and thereby characterise those disorders. In the case of MSERs this would require a somewhat spatially sparse stimulus permitting particular interaction distances between neighbouring stimuli to be well characterised, and or for comparison with non-sparse, that is spatially crowed, stimuli. Thus, both more reliable neural responses and the capacity to characterise disorders affecting lateral masking could potentially be afforded by stimuli that had fewer neighbours, that is, that were spatially sparse.

Conventional methods for estimating MSERs tend to use a binary modulation of the temporal stimuli presented. For example Sutter, E (U.S. Pat. No. 4,846,567) claims particular utility of binary m-sequences, and Malov I (WO 01/39659) claims the utility of Gold, Kasami and Bent binary sequences. In both inventions the claim is that is ideal to rapidly modulate the signals between two states, each of which is a non-null stimulus. The basic idea is that by rapidly modulating the stimulus there are more repeated presentations of the stimuli within a test period and so the larger number of presentations should increase the signal to noise ratio in the obtained MSERs by decreasing the standard error or noise in the estimated responses. The present inventors found that by considerably lowering the presentation rate of stimuli, by introducing many null stimuli between the non-null stimuli, that the responses to those stimuli became so large that they overcame the disadvantage of having relatively fewer stimulus presentations within a given test period. These less dense stimulus sequences were termed temporally sparse stimuli (International Application Number: PCT/AUO1/00343). The beneficial effect of temporally sparse stimuli for MSERs determined from responses of the human pupil suggested by the present authors (International Application Number: PCT/AUO1/00343) has subsequently been demonstrated by Tan L., Kondo M., Sato M., Kondo N. and Miyake Y. entitled "Multifocal pupillary light response fields in normal subjects and patients with visual field defects", (2001 Vision Res, 41: 1073-1084).

An efficient way to characterise the response of neurones is through the estimation of linear and non-linear temporal functions known as kernels. These kernels can summarise linear response of the system under study and also non-linear interactions in the response. Multiple stimuli can be presented simultaneously and the responses to each characterised by separate kernels for each stimulus. For example, the present inventors in U.S. Pat. No. 6,315,414 describe a method for estimating binocular interaction kernels and their potential use in diagnosing and monitoring diseases like multiple sclerosis. The inventors also showed that those temporally sparse stimuli could be used to estimate linear and non-linear weighting functions that are Wiener or Volterra kernels by insuring that any two stimulus sequences were governed by pseudorandom sequences that were sufficiently uncorrelated (International Application Number: PCT/AUO1/00343), thus permitting MSERs to be efficiently measured through the concurrent presentation of many stimuli to the visual field.

A necessary component of the temporally sparse stimuli is that the non-null stimuli need to be presented relatively transiently, that is briefly, in order to appeal to particular neural response regulating mechanisms and produce large responses. The demonstration of the method in PCT/AUO1/00343 used stimuli with a maximum duration of 10 ms. The present authors have also used maximum durations of 13 to 27 ms per non-null stimulus. Presentation rates of the non-null stimuli at mean rates around 2 to 4 presentations per second per stimulus region produce good signal to noise ratios. One can thus understand that for a stimulus layout like that of FIG. 3, that at a mean rate of presentation of non-null stimuli of 2 to 4 per second, the chance of any stimulus region having a near neighbour display a non-null stimulus at the same time is low. Thus, on the grounds that previous demonstrations of lateral masking involved many neighbours and or slower presentation times it would be surprising if there was a significant lateral masking effect operating, and that these effects could be demonstrated with the use of pseudorandom stimuli. If significant lateral masking effects could be found then the temporally sparse stimuli could be rendered spatially sparser by careful selection of the temporal sequences in neighbouring regions, and larger and more accurate MSERs could thereby be measured. Similarly, if significant lateral masking was occurring, then modifying the nature of the spatial sparseness could accentuate the characterisation of disorders known to affect lateral masking.

Another variant of spatially sparse stimuli would be in the case of concurrent independent stimulation of the two eyes, so called dichoptic stimuli. Here the neighbours would be defined across the usual spatial dimensions and across eyes. Under this scheme each part of the visual field seen by the two eyes would be considered a pair of neighbours, and so binocular neighbours should not be concurrently stimulated. Alternatively, one might compare the effect of binocularly sparse and non-sparse stimuli in persons with defective binocular vision as in amblyopia.

From the foregoing, the present inventors considered that stimuli that could simultaneously be used to estimate some or all of the coefficients of linear and or non-linear weighting functions such as Wiener or Volterra kernels, and which could utilise the effects of lateral masking across non-temporal dimensions of a plurality of stimuli, would provide efficient, non-invasive, assessment of broad sections of the nervous system.

Given the above the present inventors hypothesised that stimuli consisting of temporally sparse pseudorandom sequences that were also arranged to be spatially sparse across the non-temporal dimensions of the stimulus ensemble would provide the following:

(a) The spatially sparse nature of the stimuli would further enhance the response size and reliability of the responses compared to temporally sparse stimuli delivered at the same rates but without consideration of the effects of near neighbours in the plurality of stimuli presented across the non-temporal dimensions of the stimulus;

(b) The recorded responses arising from neural activity being biased towards such spatially dependent response regulating mechanisms could also assist in characterising disease known to affect such spatial interactions, (c) The pseudorandom occurrence of the non-null stimuli would make the stimulus sequences sufficiently statistically rich as to permit the estimation of kernels in response to multiple stimuli thus making MSERs possible, even for quite short stimulus sequences;

In order that the invention may be readily understood and put into practical effect, particular preferred embodiments will now be described by way of the following non-limiting examples.

EXAMPLES

Example 1

Apparatus

A schematic of the basic system components forming an embodiment of the apparatus of the present invention is shown in FIG. 1. The major components are a display device presenting visual stimuli to one or both eyes, in the present non-limiting example to one eye only; a means for assessing cortical neural responses, in the present example electrodes; an amplifier for recording a visual evoked electrical potential; and a means for computing estimated coefficients of the linear and non-linear weighting functions characterising the response to the non-null stimuli. Thin arrows associate labels with objects while thick block arrows indicate the direction of information flow or control.

The test stimuli for each subject were presented on a video monitor at 75 pictures per second. Since the stimuli were presented on a video monitor it is common to refer to the sequence of pictures presented as a sequence of frames presented at a particular frame rate, in this case 75 frames per second. The layout of the plurality of stimulus regions is shown in FIG. 3. Two types of non-null stimuli were presented in each region according to pseudorandom stimulus modulation functions as illustrated in FIG. 2. The two non-null stimuli consisted of contrast-reversed versions of a 4 by 4 checkerboard pattern as shown in FIG. 4. Two different mean rates of presentation of the non-null stimuli in each of the plurality of regions were used: 4.2 and 9.4 presentations per second as illustrated in FIG. 2. The duration of each non-null stimulus was essentially the frame duration or 13.3 ms (1/75 seconds). When a given region was in the null stimulus condition it was blank at the mean luminance of the checks. The total duration of the test sequences was approximately 55 seconds, and 6 such sequences were presented to each of 10 subjects.

Subjects were asked to fixate a spot presented at the centre of the plurality of visual stimulus regions. Persons skilled in the art will recognise that other means of maintaining fixation, such as monitoring eye position could have been substituted without affecting the present demonstration. Evoked potentials were recorded with the samples being obtained synchronously with the rate of presentation of video stimuli. Faster sampling rates could have been used but for the present demonstration four samples per frame was used. Standard gold cup electrodes were placed on the scalp to record the evoked potentials. The stimulus generation scheme and the VEP recording apparatus are illustrated in FIG. 1. It should be noted, however, that the present invention is not predicated on the use of any one particular means of recording evoked neuronal responses. In this regard, persons of skill in the art will recognise that evoked neuronal responses may be recorded by means other than be measuring electrical potentials such as by recording changes in magnetic, or electromagnetic radiation, or acoustic signals, responses of the pupil or movements of the eyes. In the case of electromagnetic or acoustic monitoring means the electromagnetic either passive signals emitted by the brain, or the effects of scattering absorption, refraction or reflection of electromagnetic or acoustic energy transmitted towards or through the brain, could also be employed. The use of two or more of these monitoring means in some combination is also not excluded.

Example 2

Pseudorandom Stimulus Sequences

The relevant feature of the temporally sparse nature of the pseudorandom stimulus sequences will be better understood by inspection of FIG. 2, which illustrates 3 types of pseudorandom stimulus sequences. These stimulus sequences are representative of the temporal activity of one stimulus region within the plurality of regions making up the whole stimulus. The upper panel (A) illustrates a binary sequence where the stimulus varies between two conditions. Such stimuli can be generated with a pseudorandom number generator with an even distribution and the probability of the stimulus being in either stimulus condition at a given time step was set to ½. The series of 1 and −1 values could illustrate pseudorandom alternation between two non-null stimulus states such as the reversed contrast checkerboards of FIG. 4. We did not use these temporally dense binary stimuli, but such stimuli are in common use, and so they are presented here for purposes of comparison. Results of experiments with temporally, but not spatially, sparse stimuli compared with those of binary stimulus are given in FIG. 8. The middle panel (B) illustrates a ternary, bipolar version of a temporally sparse pseudorandom stimulus sequence. Here the stimulus has three levels including a more frequent null stimulus condition, at the middle stimulus level denoted by the level 0, and two less frequent non-null stimulus conditions, at levels above and below the null stimulus condition denoted 1 and −1. Persons of skill in the art will recognise that the markers −1, 0 and 1 in this example characterise the modulation of image contrast of one of the two fields of checks in the checkerboard stimuli of a region, with the other field of checks having at each step the opposite contrast. When a given region displayed the null stimulus, marker 0, it display no image contrast, that is, it was a featureless grey having the same luminance as the average of white and black checks in the non-null stimuli. In this case the probability of encountering the null condition was set to create a mean presentation rate of 4.2 non-null stimuli per second in each region. The third panel (C) illustrates a temporally less sparse ternary pseudorandom stimulus sequence where the probability of the non-null state was set to create a mean presentation rate of 9.4 stimuli per second. It should be noted that the particular examples shown are eight-second sections of the 55-second duration used in the present non-limiting demonstration. The stimulus sequences might just as well describe auditory stimuli where the stimulus conditions correspond to changes in sound pressure or frequency. Similarly the sequences might describe somatosensory stimuli such as changes in pressure level or frequency of a stimulus pressed against the skin or other tissue. The sparseness of the stimulus sequences would be appropriate to the modality stimulated. Such stimuli are illustrated in FIGS. 10 to 13. The stimulus sequences also do not have to have sharp rectangular transitions as shown in FIG. 2 but may be smoothed in various ways and the temporal evolution of the departures from the null stimulus may be different for different non-null stimuli.

Example 3

Spatially Sparse Sequences

FIG. 3 illustrates the two spatially sparse visual stimulus variants for two particular non-limiting embodiments described here in which the face of a video monitor was divided into 56 parts demarked by the lines. In the tests described in the figures that follow subjects observed visual stimuli presented in each of the 56 regions and evoked potentials were recorded. The non-null stimuli were black and white checkerboard patterns presented within each region as shown in FIG. 4. Each region had its contrast modulated in time by different pseudorandom sequences, each 55 seconds long. For the binary sequences of FIG. 2 white checks are considered to have contrast 1 and black checks contrast −1. Thus the temporal modulation sequences caused the checks within each of the 56 regions to flip the sign of their contrast or remain the same contrast according to the state, 1 or −1, of the binary sequence at a given time step. For ternary stimuli the null stimulus condition for each of the regions was a uniform mid-level grey luminance, defined as having contrast zero; one of the non-null conditions had alternate black and white checks as in a checkerboard, defined as contrast 1; the other non-null condition reversed the contrast of the checks, white interchanging with black, and was defined as contrast level −1. The 56 regions were modulated simultaneously in contrast according to independent stimulus sequences.

Two strategies were used to provide two variants of ensembles of stimuli that were spatially sparse. These strategies were illustrated in the two panels of FIG. 3.

The upper panel indicates spatial sparse Type I. Here the plurality of regions is divided into a tessellation of two classes of regions, A and B. The particular sets of temporally sparse stimulus sequences are arranged so that when class A regions have a probability, P, of displaying a non-null stimulus all other class A regions also have the same probability, P, of displaying a non-null stimulus. These regions can be called active regions. The alternative regions, those denoted as class B regions, had probability 0 of displaying a non-null stimuli, that is they all displayed a null stimulus. These regions could be called inactive regions. On the text frame of the stimulus sequence the roles of the regions denoted A and B reverse, that is the regions denoted class B become active with a certain probability, while the regions denoted class A become inactive. Thus on the next frame the B regions had a probability, P, of presenting a non-null stimulus while all the A regions displayed a null stimulus. The roles of the A and B type regions then alternated throughout the 55 second long pseudorandom stimulus sequences. In this way no region had a neighbour that shared an extended border that simultaneously presented a non-null stimulus.

The lower panel of FIG. 3 illustrates the second type of spatially sparse stimulus examined. In these Type II stimuli the plurality of stimulus regions was divided into a tessellation of 4 region classes, A, B, C and D. On any particular frame of the stimulus sequences only one of these classes of region could be active, that is having a probability P of displaying a non-null stimulus, while the other three region classes were inactive, that is displaying the null stimulus. As the 55-second stimulus evolved the four different region classes took turns having the possibility of being active. Notice that unlike the Type I spatially sparse stimulus the Type II stimulus means that no neighbour either sharing a border or a corner with an active region ever displays a non-null stimulus.

In an alternative embodiment the regions of the inactive class could have a probability of displaying a non-null stimulus, Q, where Q was greater than 0 but which was much less than the probability, P, of a region of the active class displaying a non-null stimulus.

Recordings were made from 10 subjects. Each subject was tested with the two types of spatially sparse stimuli illustrated in FIG. 3, Type I and Type II, and with a reference stimulus, in which the pseudorandom sequences were temporally sparse ternary sequences as in FIG. 2, but where no consideration was given to their spatial sparseness as in FIG. 4. Each subject was tested with the three spatial variants using two mean presentation rates of the non-null stimuli, 4.2 and 9.4 presentations per second. Six repeats were obtained for the resulting six stimulus conditions. In each case the same coefficients of Wiener kernels sufficient to characterise the response to the non-null stimuli were estimated from the evoked potentials. Examples are shown in FIGS. 6. The significant improvement in signal to noise ratio for the spatially sparse conditions relative to the reference stimulus at 4.2 presentations per second is given in FIG. 8. Both spatially sparse conditions had a significant ($p<0.05$) increase in signal to noise ratio (SNR) of about 0.75 dB relative to the non-spatially sparse stimulus reference design. Given that relative recording time to achieve a given level of significance will be approximately related to the power signal to noise ratio, the two spatial sparse conditions would be expected to require about 16% less recording time that a temporally sparse set of stimuli for which no consideration was given to the possible effects of simultaneously presented neighbouring non-null stimuli.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

The term "about" is used herein to refer to frequencies or probabilities that vary by as much as 30%, preferably by as much as 20%, and more preferably by as much as 10% to a reference frequency or probability.

Throughout this specification, unless the context requires otherwise, the words "comprise", "comprises" and "comprising" will be understood to imply the inclusion of a stated step or element or group of steps or elements but not the exclusion of any other step or element or group of steps or elements.

The disclosure of every patent, patent application, and publication cited herein is incorporated herein by reference in its entirety.

The citation of any reference herein should not be construed as an admission that such reference is available as "Prior Art" to the instant application Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention.

The invention claimed is:

1. A method of assessing a sensory nervous system of a subject, including:
  simultaneously presenting, using a stimulator, to two or more parts of the sensory nervous system respective sequences of spatially sparse stimuli, the stimuli being presented as a tessellation or contiguous array of adjacent neighbouring stimulus regions defined on dimensions of the sensory nervous system, the tessellation or contiguous array having borders and corners defining said stimulus regions,
  varying using a processor each sequence of stimuli of each region over time between a null stimulus and one or more less frequent non-null stimuli with the probability of a single non-null stimulus occurring of P,
  controlling using said processor the variation of each sequence of stimuli presented to neighbouring parts of the sensory nervous system so that the adjacent neighbouring stimulus regions either share a border or a corner having a probability 0 of presenting a simultaneous non-null stimulus, rendering the stimuli spatially sparse,
  measuring using a monitor each of one or more simultaneous responses by the subject to the sequences of spatially sparse stimuli, and
  determining using said processor weight functions from the simultaneous responses for assessment of the sensory nervous system.

2. The method according to claim 1, wherein the non-null stimuli appear in each sequence at a rate of about 0.25 to 25 per second.

3. The method according to claim 1, wherein the sensory nervous system is a visual system and multiple parts of a retina are presented with spatially sparse stimuli.

4. The method according to claim 1, wherein the sensory nervous system is a visual system and the sequences of stimuli include either binocular or dichoptic stimuli.

5. The method according to claim 1, wherein the sensory nervous system is an aural or tactile system and the ears or skin are presented with spatially sparse stimuli.

6. The method according to claim 1, wherein the parts of the sensory nervous system are selected from the group consisting of the retina, the ears, the skin, and the brain of the subject.

7. The method according to claim 1, wherein the spatially sparse stimuli are selected from a range of signals including light, sound frequency, and pressure.

8. The method according to claim 1, wherein the adjacent neighbouring stimulus regions are divided into classes and only one of the classes has a non-zero probability of presenting stimuli at any time.

9. The method according to claim 1, wherein the responses are nonlinear and the weight functions are Wiener or Volterra kernels.

10. The method according to claim 1, wherein the adjacent neighbouring stimulus regions are regions sharing a border that is an extended border.

11. The method according to claim 1, wherein the adjacent neighbouring stimulus regions of a given stimulus region have a probability of displaying a non-null stimulus that is larger than 0 but is much less than the probability of said given stimulus region itself displaying an active state.

12. An apparatus for assessing a sensory nervous system of a subject, including:
   a stimulator that is adapted to simultaneously present to two or more parts of the sensory nervous system respective sequences of spatially sparse stimuli, the stimuli being presented as a tessellation or contiguous array of adjacent neighbouring stimulus regions defined on dimensions of the sensory nervous system, the tessellation or contiguous array having borders and corners defining said stimulus regions;
   a monitor is adapted to measure each of one or more simultaneous responses by the subject to said sequences of spatially sparse stimuli, and
   a processor adapted to:
      vary each sequence of stimuli of each region over time between a null stimulus and one or more less probable non-null stimuli with the probability of a single non-null stimulus occurring of P,
      control the variation of each sequence of stimuli presented to neighbouring parts of the sensory nervous system so that the adjacent neighbouring stimulus regions either share a border or a corner having a probability 0 of presenting a simultaneous non-null stimulus, rendering the stimuli spatially sparse, and
      determine weight functions from the responses for assessment of the sensory nervous system.

13. The apparatus according to claim 12, wherein said monitor adapted to measure responses to said spatially sparse stimuli by way of electrode potentials on the head of the subject.

14. The apparatus according to claim 12, wherein the non-null stimuli appear in each sequence at a rate of about 0.25 to 25 per second.

15. The apparatus according to claim 12, wherein the sensory nervous system is a visual system and multiple parts of a retina are presented with spatially sparse stimuli.

16. The apparatus according to claim 12, wherein the sensory nervous system is a visual system and the sequences of stimuli include either binocular or dichoptic stimuli.

17. The apparatus according to claim 12, wherein the sensory nervous system is an aural or tactile system and the ears or skin are presented with spatially sparse stimuli.

18. The apparatus according to claim 12, wherein the parts of the sensory nervous system are selected from the group consisting of the retina, the ears, the skin, and the brain of the subject.

19. The apparatus according to claim 12, wherein the spatially sparse stimuli are selected from a range of signals including light, sound frequency, and pressure.

20. The apparatus according to claim 12, wherein the adjacent neighbouring stimulus regions are divided into classes and only one of the classes has a non-zero probability of presenting stimuli at any time.

21. The apparatus according to claim 12, wherein the responses are nonlinear and the weight functions are Wiener or Volterra kernels.

22. The apparatus according to claim 12, wherein the adjacent neighbouring stimulus regions are regions sharing a border that is an extended border.

23. The apparatus according to claim 12, wherein the adjacent neighbouring stimulus regions of a given stimulus region have a probability of displaying a non-null stimulus that is larger than 0 but is much less than the probability of said given stimulus region itself displaying an active state.

* * * * *